(12) United States Patent
Aida

(10) Patent No.: US 6,815,158 B2
(45) Date of Patent: Nov. 9, 2004

(54) METHODS FOR JUDGING RESISTANCE TO THE ONSET OF BOVINE LEUKEMIA

(75) Inventor: Yoko Aida, 3-105, Shareru Tsukuba Matsushiro, 21-2, Matsushiro 4-chome, Tsukuba-shi, Ibaraki 305-0035 (JP)

(73) Assignees: Riken, Saitama (JP); Yoko Aida, Ibaraki (JP)

( * ) Notice: Subject to any disclaimer, the term of this patent is extended or adjusted under 35 U.S.C. 154(b) by 0 days.

(21) Appl. No.: 09/794,366

(22) Filed: Feb. 28, 2001

(65) Prior Publication Data

US 2003/0091984 A1 May 15, 2003

(30) Foreign Application Priority Data

Mar. 1, 2000 (JP) ........................................ 2000-056093

(51) Int. Cl.[7] .............................. C12Q 1/70; C12Q 1/68; C12P 19/34
(52) U.S. Cl. ................................ 435/5; 435/6; 435/91.2
(58) Field of Search ................................ 435/5, 6, 91.2

(56) References Cited

U.S. PATENT DOCUMENTS

| 5,567,809 A | 10/1996 | Apple et al. |
| 5,582,987 A | 12/1996 | Lewin et al. |
| 6,090,540 A | 7/2000 | Aida |

FOREIGN PATENT DOCUMENTS

WO 98/03680 1/1998

OTHER PUBLICATIONS

Aida et al., "Tumor–associated $M_r$ 34,000 and $M_r$ 32,000 Membrane Glycoproteins that are Serine Phosphorylated Specifically in Bovine Leukemia Virus–induced Lymphosarcoma Cells", *Cancer Research*, 52:6463–6470 (1992).

Aida et al., "Phenotype and Ontogeny of Cells Carrying a Tumor–associated Antigen that is Expressed on Bovine Leukemia Virus–induced Lymphosarcoma", *Cancer Research*, 53, pp. 429–437 (1993).

Aida et al., "Identification of a New Bovine MHC Class II DRB Allele by Nucleotide Sequencing and an Analysis of Phylogenetic Relationships," *Biochemical and Biophysical Research Communications*, vol. 209, No. 3, pp. 981–988 (1995).

Aida et al., "Tumor–associated Antigens on Bovine Leukemia Virus–induced Bovine Lymphosarcoma Identified by Monoclonal Antibodies", *Cancer Research*, 45, pp. 1174–1180 (1985).

Miyasaka et al., "Sheep as an Experimental Model for Immunology: Immunological Techniques in Vitro and in Vivo", *Immunological Methods*, vol. III, pp. 403–423 (1985).

Aida et al., "Cloning of cDNAs and Molecular Evolution of a Bovine MHC Class II DRA Gene", *Biochem. Biophys. Res. Commun.*, 204, pp. 195–202 (1994).

Armstrong et al., "Preferential Site–dependent Cleavage by Restriction Endonuclease PstI", *Nucleic Acids Research*, vol. 10, No. 3, pp. 993–1007 (1982).

Brooker, *Genetics Analysis and Principles*, p. 79 (1999).

(List continued on next page.)

*Primary Examiner*—Hankyel T. Park
(74) *Attorney, Agent, or Firm*—Greenblum & Bernstein, P.L.C.

(57) ABSTRACT

A method for judging a resistance to the onset of bovine leukemia caused by bovine leukemia virus BLV, wherein a bovine individual, in which amino acids specified by the amino acid numbers 74, 77 and 78 of β1 domain of bovine MHC Class II DRβ chain are Glu, Arg and Val, respectively, is judged to have a resistance to the onset of the leukemia.

5 Claims, 2 Drawing Sheets

OTHER PUBLICATIONS

Hughes et al., "Proviruses of Avian Sarcoma Virus are Terminally Redundant, Co–extensive with Unintegrated Linear DNA and Integrated at Many Sites", *Cell,* vol. 15, pp. 1397–1410 (1978).

Levy et al., "Bovine Leukemia Virus Specific Antibodies Among French Cattle. I. Comparison of Complement Fixation and Hematological Tests", *Int. J. Cancer,* 19, 882–827 (1977).

McKnight, "The Induction of Ovalbumin and Conalbumin mRNA by Estrogen and Progesterone in Chick Oviduct Explant Cultures", *Cell,* vol. 14, pp. 403–413 (1978).

Stone et al., "Up–regulation of IL–2 Receptor α and MHC Class II Expression on Lymphocyte Subpopulations from Bovine Leukemia Virus Infected Lymphocytotic Cows", *Veterinary Immunology and Immunopathology,* 48, pp. 65–76 (1995).

Stone et al., "Modulation of Bovine Leukemia Virus–associated Spontaneous Lymphocyte Proliferation by Monoclonal Antibodies to Lymphocyte Surface Molecules", *Clinical Immunology and Immunovirology,* vol. 83, No. 2, pp. 156–164 (1997).

"Enzootic Bovine Leukosis", Alberta Agriculture Food and Rural Development, www.agric.gov.ab.ca/agdex/600/63–07.html, pp. 1–4 (1996).

Xu et al., "Polymorphism in BoLA–DRB3 exon 2 correlates with resistance to persistent lymphocytosis caused by bovine leukemia virus", Journal of Immunology, Williams & Wilkins Co., US, vol. 151, No. 12, Dec. 15, 1993, pp.6977–85.

Lewin et al., "PCR Primer for Amplifying BOLA–DRB3 Bovine Allele", EMBL., XP002194085.

Lewin et al., "PCR Primer for Amplifying BOLA–DRB3 Bovine Allele", EMBL., XP002194084.

Lewin et al., "Disease Resistance and Immune Response Genes in Cattle: Strategies for their Existence" Journal of Diary Science American Diary Science Association, Champaign, Illinois, US, vol. 72, No. 5, May 1989, pp. 1334–1348.

Fig. 1

| | | n=86 | % | 9 | 11 | 12 | 13 | 24 | 26 | 28 | 30 | 31 | 32 | 37 | 45 | 47 | 55 | 56 | 57 | 59 | 60 | 61 | 65 | 66 | 67 | 70 | 71 | 74 | 77 | 78 | 81 | 85 | 86 |
|---|---|---|---|---|---|---|---|---|---|---|---|---|---|---|---|---|---|---|---|---|---|---|---|---|---|---|---|---|---|---|---|---|---|
| Healthy | 0101 | 4 | 4.7 | E | S | K | S | V | F | L | D | Y | Y | T | T | G | F | R | Q | D | E | Y | W | D | F | E | K | E | R | V | H | G | M |
| | 1401 | 7 | 8.1 | Q | H | - | G | - | L | - | - | H | F | Y | F | D | - | - | P | A | - | Q | - | - | - | Q | - | - | - | - | - | - | V |
| | 0701 | 7 | 8.1 | - | C | - | R | - | - | - | - | C | F | H | F | - | - | - | R | V | - | Q | - | - | - | - | R | - | - | - | - | V | V |
| | 0902 | 5 | 5.8 | - | - | - | - | - | - | - | - | E | S | F | Y | N | - | Y | - | P | - | - | - | - | E | I | - | R | - | - | - | - | V | G |
| | 2703 | 2 | 2.3 | - | Y | N | - | - | - | D | C | - | T | - | G | F | R | P | D | E | Y | W | K | - | - | - | R | - | - | - | - | V | G |
| | 1101 | 6 | 7.0 | Q | H | - | G | - | L | - | - | H | F | Y | Y | D | - | - | P | S | - | - | - | - | - | - | R | R | - | T | - | - | V | V |
| | 0501 | 1 | 1.2 | - | H | - | - | L | Y | - | - | - | F | Y | Y | - | Y | - | P | - | K | - | - | E | I | R | - | N | T | Y | - | V | V |
| | 0502 | 1 | 1.2 | - | H | - | - | L | Y | D | Y | F | - | V | G | Y | R | P | D | K | Y | W | K | - | L | R | - | N | T | Y | - | V | G |
| | 0503 | 3 | 3.5 | - | - | - | - | L | Y | - | - | - | F | Y | Y | - | Y | - | P | - | K | - | - | E | I | R | - | N | T | Y | - | V | F |
| | 1302 | 7 | 8.1 | - | L | - | - | - | - | - | - | E | S | F | Y | N | - | Y | - | P | - | K | - | - | - | L | R | - | N | T | Y | - | V | V |
| | 3401 | 1 | 1.2 | - | C | - | - | - | - | - | - | E | S | F | Y | F | - | Y | - | R | V | - | Q | L | - | L | Q | - | N | T | Y | - | V | V |
| | 1601 | 13 | 15.1 | - | T | - | K | - | - | - | - | - | F | H | F | - | Y | - | P | - | K | - | - | - | - | - | - | A | T | Y | - | V | G |
| | 20012 | 1 | 1.2 | - | C | - | R | - | L | - | - | - | F | Y | R | - | - | - | P | S | - | - | - | - | - | - | Q | R | A | T | Y | - | V | V |
| | 0201 | 4 | 4.7 | - | - | T | - | - | - | - | - | - | F | H | F | - | Y | - | P | - | - | - | - | - | E | I | R | A | A | T | Y | - | - | V |
| | 1001 | 10 | 11.6 | - | - | - | - | - | - | - | - | - | F | H | Y | - | Y | Q | R | V | - | - | C | - | - | R | A | A | T | Y | - | V | G |
| | 1201 | 6 | 7.0 | - | T | - | K | - | - | - | N | - | F | H | F | - | Y | - | P | - | - | - | - | E | I | R | A | A | T | Y | - | V | G |
| | 1501 | 8 | 9.3 | - | - | T | - | - | Y | - | - | - | F | H | F | - | Y | - | R | V | - | Q | L | - | T | R | E | Y | T | Y | - | V | V |
| PL | | n=30 | | | | | | | | | | | | | | | | | | | | | | | | | | | | | | | | |
| | 0701 | 1 | 3.3 | - | C | - | R | - | - | - | - | C | F | H | F | - | - | - | R | V | - | Q | - | - | - | - | R | - | - | - | - | V | V |
| | 1101 | 1 | 3.3 | Q | H | - | G | - | L | - | - | H | F | Y | Y | D | - | - | P | S | - | - | - | - | - | - | R | R | - | T | - | - | V | V |
| | 0503 | 1 | 3.3 | - | - | - | - | L | Y | - | - | - | F | Y | Y | - | Y | - | P | - | K | - | - | E | I | R | - | N | T | Y | - | V | F |
| | 1302 | 1 | 3.3 | - | L | - | - | - | - | - | - | E | S | F | Y | N | - | Y | - | P | - | K | - | - | - | L | R | - | N | T | Y | - | V | V |
| | GH2sp6 | 1 | 3.3 | - | - | - | - | L | Y | D | Y | F | - | Y | G | Y | R | P | D | K | Y | W | K | E | I | R | - | N | T | Y | - | V | F |
| | 1601 | 14 | 46.7 | - | T | - | K | - | - | - | - | - | F | H | F | - | Y | - | P | - | K | - | - | - | - | - | - | A | T | Y | - | V | G |
| | 0201 | 1 | 3.3 | - | - | T | - | - | - | - | - | - | F | H | F | - | Y | - | P | - | - | - | - | - | E | I | R | A | A | T | Y | - | - | V |
| | 1001 | 3 | 10.0 | - | - | - | - | - | - | - | - | - | F | H | Y | - | Y | Q | R | V | - | - | C | - | - | R | A | A | T | Y | - | V | G |
| | 1201 | 1 | 3.3 | - | T | - | K | - | - | - | N | - | F | H | F | - | Y | - | P | - | - | - | - | E | I | R | A | A | T | Y | - | V | G |
| | 1501 | 5 | 16.7 | - | - | T | - | - | Y | - | - | - | F | H | F | - | Y | - | R | V | - | Q | L | - | T | R | E | Y | T | Y | - | V | V |
| | 0801 | 1 | 3.3 | - | A | T | - | - | - | D | Y | F | H | L | G | F | R | P | S | V | H | L | K | - | - | D | E | S | T | Y | - | V | V |
| Lymphoma | | n=46 | | | | | | | | | | | | | | | | | | | | | | | | | | | | | | | | |
| | 0902 | 2 | 4.3 | - | - | - | - | - | - | - | - | E | S | F | Y | N | - | Y | - | P | - | - | - | - | E | I | - | R | - | - | - | - | V | G |
| | 1101 | 3 | 6.5 | Q | H | - | G | - | L | - | - | H | F | Y | Y | D | - | - | P | S | - | - | - | - | - | - | R | R | - | T | - | - | V | V |
| | 0501 | 1 | 2.2 | - | H | - | - | L | Y | - | - | - | F | Y | Y | - | Y | - | P | - | K | - | - | E | I | R | - | N | T | Y | - | V | V |
| | 3401 | 1 | 2.2 | - | C | - | - | - | - | - | - | E | S | F | Y | F | - | Y | - | R | V | - | Q | L | - | L | Q | - | N | T | Y | - | V | V |
| | 1601 | 16 | 34.8 | - | T | - | K | - | - | - | - | - | F | H | F | - | Y | - | P | - | K | - | - | - | - | - | - | A | T | Y | - | V | G |
| | 20012 | 3 | 6.5 | - | C | - | R | - | L | - | - | - | F | Y | R | - | - | - | P | S | - | - | - | - | - | - | Q | R | A | T | Y | - | V | V |
| | 0201 | 5 | 10.9 | - | - | T | - | - | - | - | - | - | F | H | F | - | Y | - | P | - | - | - | - | - | E | I | R | A | A | T | Y | - | - | V |
| | 1001 | 11 | 23.9 | - | - | - | - | - | - | - | - | - | F | H | Y | - | Y | Q | R | V | - | - | C | - | - | R | A | A | T | Y | - | V | G |
| | 1201 | 1 | 2.2 | - | T | - | K | - | - | - | N | - | F | H | F | - | Y | - | P | - | - | - | - | E | I | R | A | A | T | Y | - | V | G |
| | m64sp3 | 1 | 2.2 | - | Y | - | - | - | - | D | Y | - | T | - | G | F | R | Q | D | E | Q | W | K | - | - | R | A | A | T | Y | Y | V | G |
| | 1501 | 2 | 4.3 | - | - | T | - | - | Y | - | - | - | F | H | F | - | Y | - | R | V | - | Q | L | - | T | R | E | Y | T | Y | - | V | V |

| Amino acid sequence (position 71~80) | Nucleotide sequence (position 231~240) | Digesten with | |
|---|---|---|---|
| 71 72 73 74 75 76 77 78 79 80 | 211                                             240 | PstI | DraIII |
| K R A E V D R V C R | AAGCGGGGCCGAGGTGGACAGGGTGTGCAGA | − | − |
| R R A E V D R V C R | -G---------------------------- | − | − |
| R R A N V D R V C R | ------------A-T---------------- | − | − |
| K R A A V D T Y C R | -----------------C-----C-TAC--- | + | − |
| K R A A V D T Y C R | ----------GC-----------C-TAC--- | + | − |
| A R A S V D T Y C R | -G-------------TTC-----C-TAC--- | + | − |
| E R A Y V D T Y C R | -G-------------T-T-----C-TAC--- | + | − |
| E R A N V D T Y C R | -G----------A-T---------C-TAC--- | + | − |
| K R A A V D T Y C R | ----------------C---------C-TAC--- | + | − |
| R R A A V D T Y C R | -G--------------------------C--- | − | − |
| R R A E V D T V C R | -G--------------------------C--- | − | + |
| K R A E V D T V C R | ----------------------------C--- | − | + |

B)

| Restricton enzyme for digesting | Primer for PCR | Digested fragment length (bp) | | | | | | |
|---|---|---|---|---|---|---|---|---|
| | | TY | TV | RV | TY/TY | TY/TV | RV/TY | RV/RV |
| PstI | DRB40 | 199, 48 | 247 | 247 | 199, 48 | 247, 199, 48 | 247, 199, 48 | 247 |
| | DRB100 | 139, 48 | 187 | 187 | 139, 48 | 187, 139, 48 | 187, 139, 48 | 187 |
| DraIII | DRB40 | 247 | 194, 53 | 247 | 247 | 247, 194, 53 | 247 | 247 |
| | DRB100 | 187 | 134, 53 | 187 | 187 | 187, 134, 53 | 187 | 187 |

SEQUENCE LISTING

<160> NUMBER OF SEQ ID NOS: 19

<210> SEQ ID NO 1
<211> LENGTH: 38
<212> TYPE: DNA
<213> ORGANISM: Artificial
<220> FEATURE:
<223> OTHER INFORMATION: Description of Artificial Sequence: Synthetic
      DNA

<400> SEQUENCE: 1
tgtaaaacga cggccagtag cacatttcct gcagtatc                             38

<210> SEQ ID NO 2
<211> LENGTH: 42
<212> TYPE: DNA
<213> ORGANISM: Artificial
<220> FEATURE:
<223> OTHER INFORMATION: Description of Artificial Sequence: Synthetic
      DNA

<400> SEQUENCE: 2
tgtaaaacga cggccagtag cacatttcct ggagtattct aa                        42

<210> SEQ ID NO 3
<211> LENGTH: 39
<212> TYPE: DNA
<213> ORGANISM: Artificial
<220> FEATURE:
<223> OTHER INFORMATION: Description of Artificial Sequence: Synthetic
      DNA

<400> SEQUENCE: 3
tgtaaaacga cggccagtag cacatttcct ggagtatta                            39

<210> SEQ ID NO 4
<211> LENGTH: 39
<212> TYPE: DNA
<213> ORGANISM: Artificial
<220> FEATURE:
<223> OTHER INFORMATION: Description of Artificial Sequence: Synthetic
      DNA

<400> SEQUENCE: 4
tgtaaaacga cggccagtag cacatttcct ggagtattg                            39

<210> SEQ ID NO 5
<211> LENGTH: 36
<212> TYPE: DNA
<213> ORGANISM: Artificial
<220> FEATURE:
<223> OTHER INFORMATION: Description of Artificial Sequence: Synthetic
      DNA

<400> SEQUENCE: 5
tgtaaaacga cggccagtca catttcctgg agtatg                               36

<210> SEQ ID NO 6
<211> LENGTH: 37
<212> TYPE: DNA
<213> ORGANISM: Artificial
<220> FEATURE:
<223> OTHER INFORMATION: Description of Artificial Sequence: Synthetic
      DNA

<400> SEQUENCE: 6

```
tgtaaaacga cggccagtgc acatttcctg gagtatc                           37

<210> SEQ ID NO 7
<211> LENGTH: 38
<212> TYPE: DNA
<213> ORGANISM: Artificial
<220> FEATURE:
<223> OTHER INFORMATION: Description of Artificial Sequence: Synthetic
      DNA

<400> SEQUENCE: 7
tgtaaaacga cggccagtag cacatttcct ggagtata                          38

<210> SEQ ID NO 8
<211> LENGTH: 40
<212> TYPE: DNA
<213> ORGANISM: Artificial
<220> FEATURE:
<223> OTHER INFORMATION: Description of Artificial Sequence: Synthetic
      DNA

<400> SEQUENCE: 8
tgtaaaacga cggccagtca catttcctgg agtattctac                        40

<210> SEQ ID NO 9
<211> LENGTH: 39
<212> TYPE: DNA
<213> ORGANISM: Artificial
<220> FEATURE:
<223> OTHER INFORMATION: Description of Artificial Sequence: Synthetic
      DNA

<400> SEQUENCE: 9
caggaaacag ctatgacccg ccgctgcaca gtgaaactc                         39

<210> SEQ ID NO 10
<211> LENGTH: 28
<212> TYPE: DNA
<213> ORGANISM: Artificial
<220> FEATURE:
<223> OTHER INFORMATION: Description of Artificial Sequence: Synthetic
      DNA

<400> SEQUENCE: 10
ggaattcctc tctctgcagc acatttcc                                    28

<210> SEQ ID NO 11
<211> LENGTH: 26
<212> TYPE: DNA
<213> ORGANISM: Artificial
<220> FEATURE:
<223> OTHER INFORMATION: Description of Artificial Sequence: Synthetic
      DNA

<400> SEQUENCE: 11
tttaaattcg cgctcacctc gccgct                                      26

<210> SEQ ID NO 12
<211> LENGTH: 45
<212> TYPE: DNA
<213> ORGANISM: Artificial
<220> FEATURE:
<223> OTHER INFORMATION: Description of Artificial Sequence: Synthetic
      DNA

<400> SEQUENCE: 12
```

```
tgtaaaacga cggccagtat tcctctctct gcagcacatt tcctg        45
```

<210> SEQ ID NO 13
<211> LENGTH: 18
<212> TYPE: DNA
<213> ORGANISM: Artificial
<220> FEATURE:
<223> OTHER INFORMATION: Description of Artificial Sequence: Synthetic
      DNA

<400> SEQUENCE: 13

```
tgtaaaacga cggccagt                                      18
```

<210> SEQ ID NO 14
<211> LENGTH: 18
<212> TYPE: DNA
<213> ORGANISM: Artificial
<220> FEATURE:
<223> OTHER INFORMATION: Description of Artificial Sequence: Synthetic
      DNA

<400> SEQUENCE: 14

```
caggaaacag ctatgacc                                      18
```

<210> SEQ ID NO 15
<211> LENGTH: 29
<212> TYPE: DNA
<213> ORGANISM: Artificial
<220> FEATURE:
<223> OTHER INFORMATION: Description of Artificial Sequence: Synthetic
      DNA

<400> SEQUENCE: 15

```
ggaattcctc tctctgcagc acatttcct                          29
```

<210> SEQ ID NO 16
<211> LENGTH: 26
<212> TYPE: DNA
<213> ORGANISM: Artificial
<220> FEATURE:
<223> OTHER INFORMATION: Description of Artificial Sequence: Synthetic
      DNA

<400> SEQUENCE: 16

```
aagtcgaccg ctgcacagtg aaactc                             26
```

<210> SEQ ID NO 17
<211> LENGTH: 23
<212> TYPE: DNA
<213> ORGANISM: Artificial
<220> FEATURE:
<223> OTHER INFORMATION: Description of Artificial Sequence: Synthetic
      DNA

<400> SEQUENCE: 17

```
gagtgtcatt tcttcaacgg gac                                23
```

<210> SEQ ID NO 18
<211> LENGTH: 23
<212> TYPE: DNA
<213> ORGANISM: Artificial
<220> FEATURE:
<223> OTHER INFORMATION: Description of Artificial Sequence: Synthetic
      DNA

<400> SEQUENCE: 18

```
ggagaagagt tcgtgcgctt cga                                23
```

```
<210> SEQ ID NO 19
<211> LENGTH: 40
<212> TYPE: DNA
<213> ORGANISM: Artificial
<220> FEATURE:
<223> OTHER INFORMATION: Description of Artificial Sequence: Synthetic
      DNA

<400> SEQUENCE: 19
tgtaaaacga cggccagtct ctctctgcag cacatttcct                              40
```

METHODS FOR JUDGING RESISTANCE TO THE ONSET OF BOVINE LEUKEMIA

FIELD OF THE INVENTION

The present invention relates to a method for judging a resistance to the onset of bovine leukemia caused by bovine leukemia virus BLV.

RELATED ART

The major histocompatibility antigens (MHC antigens) are molecules involved in self-nonself differentiation in the defense mechanism of the living body against infection. They are classified into Class I molecule composed of α chain and β2M, and class II molecule composed of α chain and β chain. A groove for trapping an antigen peptide is present on the α1 and α2 domains, and also on the α1 and β1 domains. They are featured to have the T cell receptor recognize only a fragmented peptide trapped in the groove, thereby achieve cell death (cellular immunity) by CD8+ cells which have recognized the class I antigens, as well as induce mainly antibody production (humoral immunity) by CD4+ cells which have recognized the class II antigens.

The MHC genes constitute a gene group most full of polymorphism, and the locations of pockets, shapes, sizes and properties of the peptide trapping grooves are different among haplotypes. It is considered that association conditions of the trapped fragment peptides may vary depending on these differences, which decide immune response and disease sensitivity of each individual. The correlation between the MHC haplotypes and a resistance to a disease (disease insusceptibility) or a possibility of the onset of a disease (disease susceptibility) has been reported, for example, as to human immune deficiency virus (HIV), human T cell leukemia virus (HTLV) and malaria.

As for the bovine MHC (BoLA) class II genes, existence of DQA, DQB, DRA, DRB, DNA, DOB, DYA, and DYB genes has been estimated. DRB3, inter alia, which is one of the three genes (DRB1 to B3) identified on the DRB genetic locus, has been known to encode a functional protein, and existence of 73 alleles has been revealed so far. However, there is almost no report about correlation between bovine infectious diseases and the bovine MHC (BoLA) haplotypes.

In particular, as to the bovine leukemia virus (BLV), which has the gene PX that regulates virus proliferation in the same manner as the human immunodeficiency virus (HIV) and is a retrovirus most related to HTLV-I, a research group in the United States has reported the relationship between the bovine MHC (BoLA) haplotypes and continuous lymphocytosis mainly focusing disease resistance; however, its relationship with a possibility of the onset of the leukemia has not been reported. The ratio of cattle infected by this virus (infection rate in Japan) is 10–20%, and 1–2% of the infected cattle develops extremely malignant endemic bovine leukemia to die after a long latent period of 10–15 years. Therefore, economic loss of stockbreeders caused by the virus is very serious. If a possibility of the onset of cattle after BLV infection can be evaluated by the analysis of bovine MHC (BoLA) haplotypes, it becomes possible to select beforehand disease resistant cattle for bleeding, and it is expected that extremely safe cattle breeding can be continued.

The inventors of the present invention previously analyzed the structure of DRB gene locus among the bovine MHC (BoLA) class II genes, and reported the structures of DRB3 gene (BoLA-DRB3) and the gene product thereof (Biochem. Biophys. Res. Commun., 209, pp.981–988, 1995). The inventors further studied the function of the gene and found that a portion is present, whose amino acid sequence is distinctly different between cattle developing the leukemia and cattle not developing the disease, in the gene product from the second exon (β1 domain) of BoLA-DRB3 showing particularly noticeable polymorphism. They also found that the amino acid substitutions directly correlated with disease susceptibility to BLV and disease resistance. On the basis of such findings, the inventors of the present invention succeeded in providing a method for judging a resistance to the onset of bovine leukemia caused by bovine leukemia virus BLV, wherein a bovine individual, in which an amino acid specified by the amino acid number 78 of the β1 domain of the bovine MHC Class II DRβ chain is Val, is judged to have a resistance to the onset of the leukemia (International Publication WO98/3680).

DISCLOSURE OF THE INVENTION

An object of the present invention is to elucidate the relationship between the bovine leukemia virus (BLV) and the bovine MHC (BoLA) haplotypes, and to provide a method for convenient and accurate judgment of a resistance to the onset of leukemia of a bovine individual caused by the bovine leukemia virus (BLV) by means of genetic engineering techniques. More specifically, the object of the present invention is to provide a method for judgment which enables judgment with higher accuracy than that disclosed in the aforementioned International Publication WO98/3680. Another object of the present invention is to provide a primer set useful for the aforementioned method for judgment.

The inventors of the present invention made intensive studies to achieve the aforementioned objects, and found that Arg specified by the amino acid number 77 of the β1 domain of the bovine MHC Class II DRβ chain especially has an important role for a resistance to the onset of bovine leukemia. The present invention was achieved on the basis of this finding.

The present invention thus provides a method for judging a resistance to the onset of bovine leukemia caused by bovine leukemia virus BLV, wherein a bovine individual, in which an amino acid of β1 domain of bovine MHC Class II DRβ chain specified by amino acid number 74 is Glu (glutamic acid), said amino acid specified by amino acid number 77 is Arg (arginine), and said amino acid specified by amino acid number 78 is Val (valine), is judged to have a resistance to the onset of the leukemia.

The present invention further provides a method for judging a resistance to the onset of bovine leukemia caused by bovine leukemia virus BLV, wherein a bovine individual, in which an amino acid of β1 domain of bovine MHC Class II DRβ chain specified by amino acid number 71 is Lys (lysine) or Arg, said amino acid specified by amino acid number 74 is Glu, said amino acid specified by amino acid number 77 is Arg, and said amino acid specified by amino acid number 78 is Val, is judged to have a high resistance to the onset of the leukemia. According to a preferred embodiment of the aforementioned inventions, there is provided the aforementioned method which is applied to cattle infected by the bovine leukemia virus BLV.

According to another aspect of the present invention, there is provided a method for judging a resistance to the onset of bovine leukemia caused by bovine leukemia virus BLV, which comprises the steps of:

(1) amplifying a genomic DNA isolated from a bovine individual by polymerase chain reaction (PCR) to prepare a PCR product containing a DNA coding for a part or full length of β1 domain of bovine MHC Class II DRβ chain, and (2) judging that the bovine individual, in which an amino acid of the β1 domain of the bovine MHC Class II DRβ chain specified by amino acid number 74 is Glu, said amino acid specified by amino acid number 77 is Arg, and said amino acid specified by amino acid number 78 is Val in an amino acid sequence encoded by the DNA contained in the PCR product, has a resistance to the onset of the leukemia.

The present invention also provides a method for judging a resistance to the onset of bovine leukemia caused by the bovine leukemia virus BLV, which comprises the steps of:

(1) amplifying a genomic DNA isolated from a bovine individual by polymerase chain reaction (PCR) to prepare a PCR product containing a DNA coding for a part or full length of β1 domain of bovine MHC Class II DRβ chain, and (2) judging that the bovine individual, in which an amino acid of the β1 domain of the bovine MHC Class II DRβ chain specified by amino acid number 71 is Lys or Arg, said amino acid specified by amino acid number 74 is Glu, said amino acid specified by amino acid number 77 is Arg, and said amino acid specified by amino acid number 78 is Val in an amino acid sequence encoded by the DNA contained in the PCR product, has a high resistance to the onset of the leukemia.

Furthermore, the present invention provides a method for conveniently selecting a bovine individual which has a high resistance to the onset of leukemia. This method comprises the steps of:

(1) amplifying a genome DNA isolated from a bovine individual by polymerase chain reaction (PCR) using DRB40 or DRB 100 as a forward primer and SRB3 as a reverse primer to prepare a PCR product containing a DNA coding for a part or full length of β1 domain of bovine MHC Class II DRβ chain, and (2) judging that the bovine individual, in which the PCR product is not digested by PstI and DraIII, has a high resistance to the onset of the leukemia.

In the bovine individual selected by the aforementioned method, an amino acid of the β1 domain of the bovine MHC Class II DRβ chain specified by amino acid number 71 is Lys or Arg, and said amino acid specified by amino acid number 74 is Glu, said amino acid specified by amino acid number 77 is Arg, and said amino acid specified by amino acid number 78 is Val.

BRIEF EXPLANATION OF DRAWINGS

FIG. 1 depicts results obtained by determination of the base sequence of the β1 domain of the bovine MHC Class II DRβ chain of each BLV infected cattle (Japanese Black) exhibiting any one of the pathologic states, and comparison between the deduced amino acid sequences. In the figure, the figures in the top line indicate the serial numbers of the amino acid residues, and those in the left side are the ID numbers of the alleles. The amino acid residues are indicated as one letter symbols.

FIG. 2 depicts 9 kinds of amino acid sequences specified by amino acid numbers 71 to 80 of the β1 domain of the bovine MHC Class II DRβ chain obtained from 281 cattle of Japanese Black, and results of digestion of the base sequences coding for said amino acid sequences by restriction enzymes (PstI and DraIII). In the figure, (A) shows base sequences determined and their deduced amino acid sequences, and (B) shows results of treatments with the restriction enzymes.

BEST MODE FOR CARRYING OUT THE INVENTION

The method of the present invention is applied to bovine individuals, including cattle infected with the bovine leukemia virus BLV and cattle not infected with the virus, to judge a resistance to the onset of the leukemia of the individuals. Whether or not a bovine individual is infected by the bovine leukemia virus BLV can be readily verified by a test using an antibody recognizing the bovine leukemia virus BLV.

According to a preferred embodiment of the present invention, a genomic DNA of a bovine individual is isolated, and a gene coding for a part or the full length of the β1 domain of DRβ chain of the bovine MHC Class II (the second exon of DRB3 gene) is specifically amplified by the PCR method. Then, the resulting PCR product is subjected to a sequencing to deduce an amino acid sequence specified by amino acid number from 71 to 78 of the β1 domain. A bovine individual, in which an amino acid specified by amino acid number 74 is Glu, an amino acid specified by amino acid number 77 is Arg, and an amino acid specified by amino acid number 78 is Val in the resulting amino acid sequence, is judged to have a resistance to the onset of leukemia. A bovine individual, in which an amino acid specified by amino acid number 71 is Lys or Arg, an amino acid specified by amino acid number 74 is Glu, an amino acid specified by amino acid number 77 is Arg, and an amino acid specified by amino acid number 78 is Val, is judged to have a high resistance to the onset of leukemia.

When the aforementioned amino acid sequence of the β1 domain in at least one of the alleles contains the aforementioned specified amino acid residues, the bovine individual has a resistance to leukemia. For more accurate judgment, it is preferred to compare the aforementioned amino acid sequences in both of alleles (haplotypes). A bovine individual, in which an amino acid specified by amino acid number 74 is Glu, an amino acid specified by amino acid number 77 is Arg, and an amino acid specified by amino acid number 78 is Val in the aforementioned amino acid sequence (amino acid numbers 71 to 78) of both of alleles, has a high resistance to the onset of leukemia. Moreover, a bovine individual in which an amino acid specified by amino acid number 71 is Lys or Arg, an amino acid specified by amino acid number 74 is Glu, an amino acid specified by amino acid number 77 is Arg, and an amino acid specified by amino acid number 78 is Val in the aforementioned amino acid sequence (amino acid numbers 71 to 78) of both of alleles, has a particularly high resistance to leukemia.

The amino acid sequence of the β1 domain of the bovine MHC Class II DRβ chain was reported by Aida et al. (Aida, Y., et al., Biochem. Biophys. Res. Commun., 209, pp.981–988, 1995). In FIG. 1 of International Publication No. 98/3680, the structure of mRNA of the bovine MHC Class II DRβ chain (A), and the full length cDNA and the amino acid sequence of the gene product (B) are shown. In the aforementioned figure, the β1 domain is a portion specified by the amino acid sequence of the amino acid numbers from 1 to 94.

Cattle to be judged by the method according to the present invention are not particularly limited. The method may be applied to any sorts of cattle including dairy cattle, dairy and beef cattle, beef cattle, working cattle, working and beef cattle and the like so long as they have a possibility of infection by the bovine leukemia virus BLV and a possibility of developing the leukemia owing to the infection. More specifically, examples include Japanese cattle such as Japanese Black and Japanese Shorthorn, or breeds such as Holstein, Jersey, Hereford, Aberdeen Angus, and Friesian. However, breeds are not limited to these examples.

As a sample for preparing a genomic DNA from a bovine individual, peripheral blood, an organ and the like can be utilized. For example, a tissue section of the lymph node and so forth may be used as the organ. As methods for preparing genomic DNA from the sample mentioned above, any methods available to those skilled in the art can be employed. When peripheral blood leucocytes or peripheral blood lymphocytes are used as a sample, for example, the method of Hughes et al. (Hughes, S. H., Cell, 15, pp.1397–1410, 1978) may be applied. When an organ is used, for example, a frozen tissue section may be sliced by using scissors, and then treated by the sodium dodecylsulfate and phenol-chloroform method (Mcknight, G. S., Cell, 14, pp.403–413, 1978) to prepare genomic DNA. The simplified extraction of genomic DNA from cells may also be used, whose specific examples are described in the examples of International Publication No. 98/3680.

As primers used for amplifying the resulting genomic DNA by the PCR method, any primers may be used so long as they can amplify a DNA containing a gene coding for a partial amino acid sequence of amino acid numbers from 75 to 78 of the β1 domain of the DRβ chain of the bovine MHC Class II or the full length of the β1 domain.

An example of a primer set most suitably used for the methods of the present invention includes primer set (1):

A primer: 5'-TGTAAAACGACGGCCAGTCTCTCTCTG-CAGCACATTTCCT-3';

and

B primer: 5'-CAGGAAACAGCTATGACCCGCCGCTGCA-CAGTGAAACTC-3' which enables direct sequencing methods such as the cycle sequencing and the Dynabeads DNA direct sequencing.

As primer sets introduced with a restriction endonuclease cleavage site, primer set (2):

A primer: 5'-GGAATTCCTCTCTCTGCAGCACATTTCCT-3';

and

B primer: 5'-AAGTCGACCGCTGCACAGTGAAACTC-3', or primer set (3):

A primer: a primer selected from the group consisting of:

5'-GAGTGTCATTTCTTCAACGGGAC-3',

5'-GGAGAAGAGTTCGTGCGCTTCGA-3', and

5'-GGAATTCCTCTCTCTGCAGCACATTTCCT-3';

and

B primer: 5'-AAGTCGACCGCTGCACAGTGAAACTC-3' may be utilized.

In particular, by digesting PCR alleles with PstI that are amplified by using the primer set (3), and then observing differences in the resulting cleavage patterns, it can be easily judged whether or not the bovine individual is resistant to the leukemia.

Moreover, when PCR alleles amplified by using primer set (4):

A primer DRB40: 5'-GAGTGTCATTTCTTCAACGGGAC-3',

B primer SRB3: 5'-AAGTCGACCGCTGCACAGTGAAACTC-3';

or primer set (5):

A primer DRB100: 5'-GGAGAAGAGTTCGTGCGCTTCGA-3',

B primer SRB3: 5'-AAGTCGACCGCTGCACAGTGAAACTC-3';

is treated with PstI and DraIII, and the resulting amplified product is not digested, it can be easily judged that, in the bovine individual, an amino acid of the β1 domain of the bovine MHC Class II DRβ chain specified by amino acid number 71 is Lys or Arg, said amino acid specified by amino acid number 74 is Glu, said amino acid specified by amino acid number 77 is Arg, and said amino acid specified by amino acid number 78 is Val, and that the bovine individual has a high resistance to the leukemia. However, primers and primer sets which may be used for the methods of the present invention are not limited to these examples.

An amount of DNA used for the PCR method can be appropriately chosen. For example, the amount may be about 0.1 to 0.5 $\mu$g when peripheral blood leucocytes or peripheral lymphocytes are used. As sequencing methods applied to the DNA amplified as descried above (the PCR product), any methods available to those skilled in the art may be utilized. For example, the direct sequencing may preferably be used, whose specific examples are detailed in the examples of International Publication No. 98/3680.

Most of cattle are heterozygotes, and when alleles derived from father and mother cattle may have different base sequences, the direct sequencing may fail to determine which of the alleles corresponds to the target sequence. In such cases, the PCR product amplified by using the above primer set (2) may be digested with restriction enzymes EcoRI and Sal I, and then subcloned into a vector to determine and compare the base sequence of only one of the alleles, and thereby the base sequence of the other allele may be definitely determined. To obtain more precise genetic information, it is preferred that both of the alleles from the PCR product are subcloned and each of the base sequences is determined. The specific method and applicable primers are also detailed in the examples of International Publication No. 98/3680.

EXAMPLES

The present invention will be explained more specifically by referring to examples. However, the scope of the present invention is not limited to the examples set out below. The purposes of using the primer employed in the following examples and the details of typing of the β1 domain of the bovine MHC Class II DRβ chain are described in the specification of Japanese Patent Application No. (Hei) 11-373483.

(A) Materials and Methods
(1) PCT-SBT Method
In 50 $\mu$l of ×1 rTaq buffer [10 mM Tris-HCl, 50 mM KCl, 0.1% TritonX-100] containing 120 $\mu$M each dNTP, 1.5 mM MgCl$_2$, 0.2 $\mu$M each primer, and 2 units of recombinant Ta1 DNA elongation enzyme (rTaq) (TOYOBO), 20 to 40 $\mu$g of the genome DNA prepared by the simplified extraction from a bovine individual was dissolved. Denaturation treatment was performed at 95° C. for 5 minutes, and then 20 cycles of treatment was performed, each of which cycle consisting of treatments at 95° C. for 40 seconds, at 60° C. for 30 seconds, and at 72° C. for 40 seconds. Then, elongation was made at 72° C. for 2 minutes. Primers capable of specifically amplifying the second exon of the DRB3 gene coding for the β1 domain of the bovine MHC Class II DRβ chain (BoLA-DRβ) through the PCR were used as primers.

ERB3N: 5'-GGA ATT CCT CTC TCT GCA GCA CAT TTC C-3'

HL031: 5'-TTT AAA TTC GCG CTC ACC TCG CCG CT-3'

A part of the product obtained in the aforementioned PCR (1 μl) was amplified by the PCR (PCR-SSP) method using 8 kinds of allele group-specific primers and a forward primer capable of amplifying all the alleles. The GeneAmp® Gold Buffer (25 μl, ×1) containing 120 μM each dNTP, 1.5 mM MgCl$_2$, 0.2 μM the allele group specific primer, 200 μM the reverse primer, 1 unit of AmpliTaq Gold™ DNA elongation enzyme (PE Biosystems), and 1 μl of the aforementioned PCR product was subjected to denaturation treatment at 95° C. for 10 minutes, then 20 cycles of treatment was performed, each of which cycle consisting of treatments at 95° C. for 1 minute, at 64° C. for 30 seconds, and then at 72° C. for 30 seconds. Then, elongation was made at 72° C. for 5 minutes.

a) Allele Group Specific Forward Primer

The alleles were divided into 8 groups according to the sequence of amino acids encoded by the BoLA-DRB3 second exon, and the following primers capable of specifically amplifying each group were designed.

sp1: 5'-TGT AAA ACG ACG GCC AGT AGC ACA TTT CCT GCA GTA TC-3' sp2: 5'-TGT AAA-ACG ACG GCC AGT AGC ACA TTT CCT GGA GTA TTC TAA-3' sp3: 5'-TGT AAA-ACG ACG GCC AGT AGC ACA TTT CCT GGA GTA TTA-3' sp4: 5'-TGT AAA ACG ACG GCC AGT AGC ACA TTT CCT GGA GTA TTG-3' sp5: 5'-TGT AAA ACG ACG GCC AGT CAC ATT TCC TGG AGT ATG-3' sp6: 5'-TGT AAA ACG ACG GCC AGT GCA CA TTT CCT GGA GTA TC-3' sp7: 5'-TGT AAA ACG ACG GCC AGT AGC ACA TTT CCT GGA GTA TA-3' sp8: 5'-TGT AAA ACG ACG GCC AGT CAC A TTT CCT GGA GTA TTC TAC-3' b) Forward Primer Capable of Amplifying All the Allele Groups

DRB3ALL: 5'-TGT AAA ACG ACG GCC AGT ATT CCT CTC TCT GCA GCA CAT TTC CTG-3' c) Reverse Primer

The following primer was designed as a primer capable of amplifying all the alleles.

DRB3B: 5'-CAG GAA ACA GCT ATG ACC CGC CGC TGC ACA GTG AAA CTC-3'

The PCR product was subjected to electrophoresis on 2% agarose gel and stained with ethidium bromide. The base sequence was determined by means of the following sequence primers using the PCR product obtained by the primer capable of amplifying all the alleles when only a single band of the amplified product was detected, or using two of the PCR products when two amplified products were detected.

M13(-21): 5'-TGT AAA ACG ACG GCC AGT-3'

M13rev: 5'-CAG GAA ACA GCT ATG ACC-3'

Each 1 μl of the PCR products was subjected to the sequence reaction using BigDye™ Terminator Cycle Sequencing Ready Reaction Kit (PE Biosystems) and half BD (GENPAK Ltd.). The PCR product (1 μl), 1 μl of 3 pmol the primer, 1 μl of Terminator Ready Reaction Mix, 3 μl of half BD, and 4 μl of sterilized water were mixed, and the mixture was subjected to 25 cycles of the treatment each of which cycle consisting of treatments at 96° C. for 10 seconds, at 50° C. for 5 seconds, and at 60° C. for 4 minutes according to the conditions described in the attached manual. The mixture was precipitated with ethanol according to the manual, dissolved in 10 μl of TSR for the ABI310 sequencer, and sequenced by ABI310 (PE Biosystems). The base sequences of each allele were identified by referring to those registered in the database to determine the alleles.

(2) PCR-RFLP Method (a) By using DRB40 (5'-GAG TGT CAT TTC TTC AAC GGG AC-3') as the forward primer which forms the complementary chain to the bases of the numbers 40 to 62 of the β1 domain of the bovine MHC Class II DRβ chain, and SRB3 as the reverse primer, the genomic DNA prepared by the simplified extraction from a bovine individual was amplified by PCR. After heat denaturation at 94° C. for 4 minutes, 30 cycles of the amplification was performed, each of which cycle consisting of denaturation (94° C.) for 4 minutes, annealing (63° C.) for 2 minutes, and elongation (72° C.) for 2 minutes. Final elongation (72° C.) was carried out for 10 minutes. Amplification of the PCR product having 247 bp was expected.

(b) By using DRB100 (5'-GGA GAA GAG TTC GTG CGC TTC GA-3') as the forward primer which forms a complementary chain to bases of the numbers 100 to 122 of the β1 domain of the bovine MHC Class II DRβ chain, and SRB3 as the reverse primer, the genomic DNA prepared by the simplified extraction from a bovine individual was amplified by PCR. After heat denaturation at 94° C. for 4 minutes, 30 cycles of the amplification was performed, each of which cycle consisting of denaturation (94° C.) for 1 minute, annealing (66° C.) for 2 minutes, and elongation (72° C.) for 2 minutes. Final elongation (72° C.) was carried out for 10 minutes. Amplification of the PCR product having 187 bp was expected. The PCR products obtained in (a) and (b) were digested with 2U PstI or 4U DraIII at 37° C. for 2 hours, and then the fragments were subjected to electrophoresis using a 5% agarose gel to identify cleavage patterns.

(B) Results (1) PCT-SBT Method

The base sequences of the β1 domain of the MHC Class II DRβ chain of BLV infected cattle (Japanese Black) showing different pathologic states were determined. Amino acids of the β1 domain of the bovine MHC Class II DRβ chain derived from cattle infected by the bovine leukemia virus BLV but not developing the leukemia [15 cattle with lymphocytosis (pre-cancer state: PL), and 43 cattle not developing the leukemia (antibody positive healthy cattle not developing the disease: Healthy)] were compared with those derived from cattle already developing the leukemia (23 cattle: Lymphoma). As a result, significantly higher frequency of alleles of 0701, 1302, and 1401 was observed in the healthy cattle not developing the diseases than in the cattle already developing the leukemia. On the other hand, in PL and the cattle already developing the diseases, significantly higher frequency of 1601 was observed than in the healthy cattle not developing the disease. In the cattle already developing the disease, significantly higher frequency of 1001 was observed (Table 1). The infectious conditions were classified on the basis of the criterion by Levy et al. (Levy, D., et al., Int. J. Cancer, 19, pp.822–827, 1977) and that by Aida et al. (Aida, Y., et al., Cancer Res., 52, pp.6463–6470, 1992)

and frequency as %. In the figure, amino acid residues are represented by one letter symbols. Between the cattle with developed disease and those not developing the disease, a difference was recognized in the specific amino acid sequences (the sequence specified by amino acids at the 71-, 74-, 77- and 78-positions: motif) of the β1 domain where polymorphism is most frequent observed in the β chain.

Then, frequencies of the motifs were calculated. As a result, frequency of the allele in which the amino acids at the 71-, 74-, 77- and 78-positions were Lys/Arg (K/R), Glu (E), Arg (R) and Val (V), respectively, was significantly higher in the cattle not developing the disease than in the PL cattle or the cattle already developing the disease. On the other hand, the frequency of the allele having $Ala^{71}$, $Ala/Asp^{74}$, $Thr^{77}$, and $Tyr^{78}$ was significantly higher in the PL cattle or the cattle already developing the disease than in the healthy

TABLE 1

| Allele | BLV-infected cattle with | | | | | | | | |
|---|---|---|---|---|---|---|---|---|---|
| | Normal (n = 400) | | healthy (n = 86) | | PL (n = 30) | | lymphoma (n = 46) | P values (vs. healthy) | |
| (DRB3*) | n | % | n | % | n | % | n | % | PL | lymphoma |
|---|---|---|---|---|---|---|---|---|---|---|
| 0101 | 14 | 3.5 | 4 | 4.7 | 0 | 0 | 0 | 0 | 0.2966 | 0.1758 |
| 0201 | 18 | 4.5 | 4 | 4.7 | 1 | 3.3 | 5 | 10.9 | 0.6143 | 0.1612 |
| 0501 | 2 | 0.5 | 1 | 1.2 | 0 | 0 | 1 | 2.2 | 0.7414 | 0.5773 |
| 0502 | 12 | 3.0 | 1 | 1.2 | 0 | 0 | 0 | 0 | 0.7414 | 0.6515 |
| 0503 | 10 | 2.5 | 3 | 3.5 | 1 | 3.3 | 0 | 0 | 0.7254 | 0.2732 |
| 0701 | 19 | 4.8 | 7 | 8.1 | 1 | 3.3 | 0 | 0 | 0.3373 | 0.0456 |
| 0801 | 4 | 1.0 | 0 | 0 | 1 | 3.3 | 0 | 0 | 0.2586 | — |
| 0901 | 7 | 1.8 | 0 | 0 | 0 | 0 | 0 | 0 | — | — |
| 0902 | 29 | 7.3 | 5 | 5.8 | 0 | 0 | 2 | 4.3 | 0.2171 | 0.5350 |
| 1001 | 70 | 17.5 | 10 | 11.6 | 3 | 10.0 | 11 | 23.9 | 0.5539 | 0.0581 |
| 1101 | 44 | 11.0 | 6 | 7.0 | 1 | 3.3 | 3 | 6.5 | 0.4177 | 0.6148 |
| 1201 | 34 | 8.5 | 6 | 7.0 | 1 | 3.3 | 1 | 2.2 | 0.4177 | 0.2291 |
| 1302 | 20 | 5.0 | 7 | 8.1 | 1 | 3.3 | 0 | 0 | 0.3373 | 0.0456 |
| 1401 | 8 | 2.0 | 7 | 8.1 | 0 | 0 | 0 | 0 | 0.1152 | 0.0456 |
| 1501 | 31 | 7.8 | 8 | 9.3 | 5 | 16.7 | 2 | 4.3 | 0.9203 | 0.2551 |
| 1601 | 51 | 12.8 | 13 | 15.1 | 14 | 46.7 | 16 | 34.8 | 0.0008 | 0.0095 |
| 20012 | 5 | 1.3 | 1 | 1.2 | 0 | 0 | 3 | 6.5 | 0.7414 | 0.1216 |
| 2703 | 6 | 1.5 | 2 | 2.3 | 0 | 0 | 0 | 0 | 0.5480 | 0.4227 |
| 3401 | 1 | 0.3 | 1 | 1.2 | 0 | 0 | 1 | 2.2 | 0.7414 | 0.5773 |
| m64sp3 | 5 | 1.3 | 0 | 0 | 0 | 0 | 1 | 2.2 | — | 0.3485 |
| GH2sp6 | 0 | 0.0 | 0 | 0 | 1 | 3.3 | 0 | 0 | 0.2586 | — |
| m40sp6 | 2 | 0.5 | 0 | 0 | 0 | 0 | 0 | 0 | — | — |
| m2sp3 | 3 | 0.8 | 0 | 0 | 0 | 0 | 0 | 0 | — | — |
| new3-1 | 2 | 0.5 | 0 | 0 | 0 | 0 | 0 | 0 | — | — |
| u00127 | 5 | 1.3 | 0 | 0 | 0 | 0 | 0 | 0 | — | — |

Then, the deduced amino acid sequences were compared with each other. FIG. 1 shows the ID numbers and the amino acid residues of each allele from the β1 domain of the bovine MHC Class II DRβ chain. The figure shows the amino acid residues, within the range of the amino acid numbers from 9 to 86 of the β1 domain of the bovine MHC Class II DRβ chain, which gave different amino acid sequences among the alleles. The figures on the left side indicate the ID numbers of the alleles, and the numbers of the allele are shown as n cattle not developing the disease (Table 2). In the table, $K^{71}E^{74}R^{77}V^{78}$ means that the amino acid of the β1 domain of the bovine MHC Class II DRβ chain specified by the amino acid number 71 is Lys, the amino acid specified by the amino acid number 74 is Glu, the amino acid specified by the amino acid number 77 is Arg, and the amino acid specified by the amino acid number 78 is Val. Other symbols are similarly described.

TABLE 2

| | BLV-infected cattle with | | | | | | | |
|---|---|---|---|---|---|---|---|---|
| | healthy (n = 86) | | PL (n = 30) | | lymphoma (n = 46) | | P values (vs. healthy) | |
| Epitope | n | % | n | % | n | % | PL | lymphoma |
| $V^{78}$ | 31 | 36.0 | 2 | 6.7 | 5 | 10.9 | 0.0011 | 0.0013 |
| Non-$V^{78}$ ($Y^{78}$) | 55 | 64.0 | 28 | 93.3 | 41 | 89.1 | 0.0011 | 0.0013 |

TABLE 2-continued

| | BLV-infected cattle with | | | | | | |
|---|---|---|---|---|---|---|---|
| | healthy (n = 86) | | PL (n = 30) | | lymphoma (n = 46) | P values (vs. healthy) | |
| Epitope | n | % | n | % | n | % | PL | lymphoma |
| $R^{77}$ | 25 | 29.1 | 1 | 3.3 | 2 | 4.3 | 0.0018 | 0.0004 |
| Non-$R^{77}$ ($T^{77}$) | 61 | 70.9 | 29 | 96.7 | 44 | 95.7 | 0.0018 | 0.0004 |
| $E^{74}$ | 31 | 36.0 | 2 | 6.7 | 5 | 10.9 | 0.0011 | 0.0013 |
| Non-$E^{74}$ ($N^{74}$) | 13 | 15.1 | 3 | 10.0 | 2 | 4.3 | 0.3601 | 0.0525 |
| ($A^{74}$) | 34 | 39.5 | 19 | 63.3 | 37 | 80.4 | 0.0206 | 5.1E-06 |
| ($Y^{74}$) | 8 | 9.3 | 5 | 16.7 | 2 | 4.3 | 0.9203 | 0.2551 |
| ($S^{74}$) | 0 | 0 | 1 | 3.3 | 0 | 0 | 0.2586 | — |
| $K^{71}$ | 37 | 43.0 | 17 | 56.7 | 18 | 39.1 | 0.1407 | 0.4037 |
| Non-$K^{71}$ ($R^{71}$) | 21 | 24.4 | 2 | 6.7 | 8 | 17.4 | 0.0270 | 0.2416 |
| ($A^{71}$) | 20 | 23.3 | 5 | 16.7 | 18 | 39.1 | 0.3163 | 0.9822 |
| ($E^{71}$) | 8 | 9.3 | 6 | 20.0 | 2 | 4.3 | 0.9648 | 0.2551 |
| $R^{77}V^{78}$ | 25 | 29.1 | 1 | 3.3 | 2 | 4.3 | 0.0018 | 1.81E-05 |
| $T^{77}V^{78}$ | 6 | 7.0 | 1 | 3.3 | 3 | 6.5 | 0.4177 | 0.6148 |
| $T^{77}Y^{78}$ | 55 | 64.0 | 28 | 93.3 | 41 | 89.1 | 0.0011 | 0.0013 |
| $E^{74}R^{77}V^{78}$ | 25 | 29.1 | 1 | 3.3 | 2 | 4.3 | 0.0002 | 0.0004 |
| $E^{74}T^{77}V^{78}$ | 6 | 7.0 | 1 | 3.3 | 3 | 6.5 | 0.4177 | 0.6148 |
| $A^{74}T^{77}Y^{78}$ | 34 | 39.5 | 19 | 63.3 | 37 | 80.4 | 0.0206 | 5.1E-06 |
| $Y^{74}T^{77}Y^{78}$ | 8 | 9.3 | 5 | 16.7 | 2 | 4.3 | 0.9203 | 0.2551 |
| $N^{74}T^{77}Y^{78}$ | 13 | 15.1 | 3 | 10.0 | 2 | 4.3 | 0.3601 | 0.0525 |
| $S^{74}T^{77}Y^{78}$ | 0 | 0 | 1 | 3.3 | 0 | 0 | 0.2586 | — |
| $K^{71}E^{74}R^{77}V^{78}$ | 11 | 12.8 | 0 | 0 | 0 | 0 | 0.0311 | 0.0071 |
| $R^{71}E^{74}R^{77}V^{78}$ | 14 | 16.3 | 1 | 3.3 | 2 | 4.3 | 0.0574 | 0.0368 |
| $R^{71}E^{74}T^{77}V^{78}$ | 6 | 7.0 | 1 | 3.3 | 3 | 6.5 | 0.4177 | 0.6148 |
| $A^{71}A^{74}T^{77}Y^{78}$ | 20 | 23.3 | 5 | 16.7 | 18 | 39.1 | 0.3163 | 0.9822 |
| $K^{71}A^{74}T^{77}Y^{78}$ | 13 | 15.1 | 14 | 46.7 | 16 | 34.8 | 0.0008 | 0.0095 |
| $R^{71}A^{74}T^{77}Y^{78}$ | 1 | 1.2 | 0 | 0 | 3 | 6.5 | 0.7414 | 0.1216 |
| $E^{71}Y^{74}T^{77}Y^{78}$ | 8 | 9.3 | 5 | 16.7 | 2 | 4.3 | 0.9203 | 0.2551 |
| $K^{71}N^{74}T^{77}Y^{78}$ | 13 | 15.1 | 3 | 10.0 | 2 | 4.3 | 0.3601 | 0.0525 |
| $E^{71}S^{74}T^{77}Y^{78}$ | 0 | 0 | 1 | 3.3 | 0 | 0 | 0.2586 | — |

When the frequency of genotypes was examined, significantly higher frequency of individuals having at least one allele in which the amino acids at the 74-, 77- and 78-positions were Glu, Arg, and Val, respectively, was found in the healthy cattle not developing the disease than in the PL cattle and the cattle already developing the disease. The frequency of individuals, having the allele in which the amino acid at the 71-position was Lys or Arg in the aforementioned allele of at least one side of both alleles, was higher than that in the PL cattle or the cattle already developing the disease. Whilst the frequency of individuals having the alleles with $Ala^{74}$, $Thr^{77}$, and $Tyr^{78}$ in homozygosity was significantly higher in the healthy cattle not developing the disease than in the cattle already developing the disease. In these alleles, the amino acid at the 71-position was Ala or Lys, and the frequency of the individual having the alleles coding for the amino acids of $Ala^{71}$, $Ala^{74}$, $Thr^{77}$, and $Tyr^{78}$ in homozygosity was higher in the cattle already developing the disease.

The frequency of individual having the alleles coding for the amino acids of $Lys^{71}$, $Ala^{74}$, $Thr^{77}$ and $Tyr^{78}$ in homozygosity was higher in the PL cattle. Furthermore, the frequency of individuals having these two alleles in heterozygosity was significantly higher in the cattle already developing the disease. Whilst the frequency of individuals having the alllele with $Ala^{74}$, $Thr^{77}$ and $Tyr^{78}$ and that with $Glu^{74}$, $Arg^{77}$ and $Val^{78}$ in heterozygosity was significantly higher in the healthy cattle not developing the disease. From these results, it was concluded that the individuals having the allele with $Glu^{74}$, $Arg^{77}$ and $Val^{78}$, particularly the allele with Lys/$Arg^{71}$, $Glu^{74}$, $Arg^{77}$ and $Val^{78}$, were resistant of leukemia caused by BLV.

TABLE 3

| | BLV-infected cattle with | | | | | | |
|---|---|---|---|---|---|---|---|
| | healthy (n = 43) | | PL (n = 15) | | lymphoma (n = 23) | P values (vs. healthy) | |
| | n | % | n | % | n | % | PL | lymphoma |
| RV/RV or non-RV | 22 | 51.2 | 1 | 6.7 | 2 | 8.7 | 0.0019 | 0.0005 |
| TV/TV or non-TV | 6 | 14.0 | 1 | 6.7 | 3 | 13.0 | 0.4113 | 0.6173 |
| TY/TY or non-TY | 39 | 90.7 | 15 | 100.0 | 23 | 100.0 | 0.2909 | 0.1712 |
| ERV/ERV or Non-ERV | 22 | 51.2 | 2 | 13.3 | 2 | 8.7 | 0.0098 | 0.0005 |
| ERV/Non-ERV | 19 | 44.2 | 2 | 13.3 | 2 | 8.7 | 0.0298 | 0.0025 |
| ETV/ETV or Non-ETV | 6 | 14.0 | 0 | 0 | 3 | 13.0 | 0.1506 | 0.6173 |
| ATY/ATY or Non-ATY | 28 | 65.1 | 14 | 93.3 | 21 | 91.3 | 0.0317 | 0.0178 |
| ATY/Non-ATY | 22 | 51.2 | 10 | 66.7 | 5 | 21.7 | 0.2314 | 0.0186 |
| NTY/NTY or Non-NTY | 12 | 27.9 | 3 | 20.0 | 2 | 8.7 | 0.4083 | 0.0620 |

TABLE 3-continued

| | BLV-infected cattle with | | | | | | P values (vs. healthy) | |
|---|---|---|---|---|---|---|---|---|
| | healthy (n = 43) | | PL (n = 15) | | lymphoma (n = 23) | | | |
| | n | % | n | % | n | % | PL | lymphoma |
| YTY/YTY or Non-YTY | 8 | 18.6 | 5 | 33.3 | 2 | 8.7 | 0.9343 | 0.2445 |
| STY/STY or Non-STY | 0 | 0 | 1 | 6.7 | 0 | 0 | 0.2586 | — |
| ERV/ERV | 3 | 7.0 | 0 | 0 | 0 | 0 | 0.4000 | 0.4987 |
| ERV/ATY | 10 | 23.3 | 2 | 13.3 | 1 | 4.3 | 0.3397 | 0.0464 |
| ERV/NTY | 5 | 11.6 | 0 | 0 | 1 | 4.3 | 0.2101 | 0.3108 |
| ERV/YTY | 3 | 7.0 | 0 | 0 | 0 | 0 | 0.4000 | 0.2697 |
| ERV/ETV | 1 | 2.3 | 0 | 0 | 0 | 0 | 0.7414 | 0.6515 |
| ETV/ATY | 3 | 7.0 | 0 | 0 | 3 | 13.0 | 0.4000 | 0.3456 |
| ETV/NTY | 2 | 4.7 | 0 | 0 | 0 | 0 | 0.5463 | 0.4210 |
| ATY/ATY | 6 | 14.0 | 5 | 33.3 | 16 | 69.6 | 0.9750 | 8.8E-06 |
| ATY/NTY | 4 | 9.3 | 2 | 13.3 | 0 | 0 | 0.8275 | 0.1712 |
| ATY/YTY | 5 | 11.6 | 4 | 26.7 | 1 | 4.3 | 0.9588 | 0.3108 |
| ATY/STY | 0 | 0 | 1 | 6.7 | 0 | 0 | 0.2586 | — |
| NTY/NTY | 1 | 2.3 | 0 | 0 | 0 | 0 | 0.7414 | 0.6515 |
| NTY/YTY | 0 | 0 | 1 | 6.7 | 1 | 4.3 | 0.2586 | 0.3485 |
| KERV/KERV or non-KERV | 10 | 23.3 | 0 | 0 | 0 | 0 | 0.0367 | 0.0091 |
| KERV/non-KERV | 9 | 20.9 | 0 | 0 | 0 | 0 | 0.0530 | 0.0152 |
| RERV/RERV or Non-RERV | 13 | 30.2 | 1 | 6.7 | 2 | 8.7 | 0.0618 | 0.0418 |
| RERV/Non-RERV | 12 | 27.9 | 1 | 6.7 | 2 | 8.7 | 0.0845 | 0.0620 |
| RETV/RETV or Non-RETV | 6 | 14.0 | 1 | 6.7 | 3 | 13.0 | 0.4113 | 0.6173 |
| KATY/KATY or Non-KATY | 13 | 30.2 | 11 | 73.3 | 14 | 60.9 | 0.0045 | 0.0159 |
| KATY/Non-KATY | 13 | 30.2 | 8 | 53.3 | 12 | 52.2 | 0.0994 | 0.0694 |
| AATY/AATY or Non-AATY | 19 | 44.2 | 5 | 33.3 | 14 | 60.9 | 0.3366 | 0.1507 |
| AATY/Non-AATY | 18 | 41.9 | 5 | 33.3 | 10 | 43.5 | 0.3959 | 0.6521 |
| KNTY/KNTY or Non-KNTY | 12 | 27.9 | 3 | 20.0 | 1 | 4.3 | 0.4083 | 0.0190 |
| EYTY/EYTY or Non-EYTY | 7 | 16.3 | 5 | 33.3 | 2 | 8.7 | 0.9579 | 0.3256 |

TABLE 4

| | BLV-infected cattle with | | | | | | P values (vs. healthy) | |
|---|---|---|---|---|---|---|---|---|
| | healthy (n = 43) | | PL (n = 15) | | lymphoma (n = 23) | | | |
| | n | % | n | % | n | % | PL | lymphoma |
| KERV/KERV | 1 | 2.3 | 0 | 0 | 0 | 0 | 0.7414 | 0.6515 |
| KERV/RERV | 1 | 2.3 | 0 | 0 | 0 | 0 | 0.7414 | 0.6515 |
| KERV/AATY | 2 | 4.7 | 0 | 0 | 0 | 0 | 0.5463 | 0.4210 |
| KERV/KNTY | 3 | 7.0 | 0 | 0 | 0 | 0 | 0.4000 | 0.2697 |
| KERV/EYTY | 2 | 4.7 | 0 | 0 | 0 | 0 | 0.5463 | 0.4210 |
| KERV/KATY | 1 | 2.3 | 0 | 0 | 0 | 0 | 0.7414 | 0.6515 |
| RERV/RERV | 1 | 2.3 | 0 | 0 | 0 | 0 | 0.7414 | 0.6515 |
| RERV/RETV | 1 | 2.3 | 0 | 0 | 0 | 0 | 0.7414 | 0.6515 |
| RERV/KATY | 4 | 9.3 | 1 | 6.7 | 0 | 0 | 0.6141 | 0.1712 |
| RERV/AATY | 3 | 7.0 | 0 | 0 | 1 | 4.3 | 0.4000 | 0.5651 |
| RERV/KNTY | 2 | 4.7 | 0 | 0 | 1 | 4.3 | 0.5463 | 0.7236 |
| RERV/EYTY | 1 | 2.3 | 0 | 0 | 0 | 0 | 0.7414 | 0.6515 |
| RETV/KATY | 0 | 0 | 1 | 6.7 | 1 | 4.3 | 0.2586 | 0.3485 |
| RETV/AATY | 3 | 7.0 | 0 | 0 | 2 | 8.7 | 0.4000 | 0.7747 |
| RETV/KNTY | 2 | 4.7 | 0 | 0 | 0 | 0 | 0.5463 | 0.4210 |
| KATY/KATY | 0 | 0 | 3 | 20.0 | 2 | 8.7 | 0.0147 | 0.1179 |
| KATY/RATY | 1 | 2.3 | 0 | 0 | 3 | 13.0 | 0.7414 | 0.1179 |
| KATY/AATY | 4 | 9.3 | 2 | 13.3 | 7 | 30.4 | 0.8275 | 0.0345 |
| KATY/KNTY | 1 | 2.3 | 1 | 6.7 | 0 | 0 | 0.4537 | 0.6515 |
| KATY/EYTY | 2 | 4.7 | 3 | 20.0 | 1 | 4.3 | 0.1031 | 0.7236 |
| AATY/AATY | 1 | 2.3 | 0 | 0 | 4 | 17.4 | 0.7414 | 0.0464 |
| AATY/KNTY | 3 | 7.0 | 1 | 6.7 | 0 | 0 | 0.7272 | 0.2697 |
| AATY/EYTY | 3 | 7.0 | 1 | 6.7 | 0 | 0 | 0.7272 | 0.2697 |
| AATY/ESTY | 0 | 0 | 1 | 6.7 | 0 | 0 | 0.2586 | — |
| KNTY/KNTY | 1 | 2.3 | 0 | 0 | 0 | 0 | 0.7414 | 0.6515 |
| KNTY/EYTY | 0 | 0 | 1 | 6.7 | 1 | 4.3 | 0.2586 | 0.3485 |

(2) PCR-RFLP Method

Base sequence of the β1 domain of the bovine MHC Class II DRβ chain was determined for each of 281 cattle of Japanese Black. As a result, 9 different sequences specified by amino acid numbers 71 to 80 (corresponding to base numbers 211 to 240 in the base sequence) were obtained (FIG. 2A). Among them, the alleles that contained $K^{71}E^{74}R^{77}V^{78}$ and $R^{71}E^{74}R^{77}V^{78}$, attributable to the resistance to the onset of leukemia, were amplified by PCR using SRB3 and DRB40 primers or SRB3 and DRB100 primers, and then the products were treated with PstI and DraIII. After the treatment, no digested product by both of the restriction enzymes was obtained, and the product was observed as a single band on an agarose gel (FIG. 2B).

What is claimed is:

1. A method for judging a resistance to the onset of bovine leukemia caused by bovine leukemia virus BLV, wherein a bovine individual, in which an amino acid of β1 domain of bovine MHC Class II DRβ chain specified by amino acid number 74 is Glu, an amino acid specified by amino acid number 77 is Arg, and an amino acid specified by amino acid number 78 is Val, is judged to have a resistance to the onset of the leukemia.

2. The method according to claim 1, wherein the bovine individual, in which an amino acid further specified by amino acid number 71 is Lys or Arg, is judged to have a high resistance to the onset of the leukemia.

3. A method for judging a resistance to the onset of bovine leukemia caused by bovine leukemia virus BLV, which comprises:

(1) amplifying a genome DNA isolated from a bovine individual by polymerase chain reaction to prepare a PCR product containing a DNA coding for a part or full length of β1 domain of bovine MHC Class II DRβ chain, and (2) judging that the bovine individual, in which an amino acid of the β1 domain of the bovine MHC Class II DRβ chain specified by amino acid number 74 is Glu, an amino acid specified by amino acid number 77 is Arg, and an amino acid specified by amino acid number 78 is Val in an amino acid sequence encoded by the DNA contained in the PCR product, has a resistance to the onset of the leukemia.

4. The method according to claim 3 wherein the bovine individual, in which an amino acid further specified by amino acid number 71 is Lys or Arg, is judged to have a high resistance to the onset of the leukemia.

5. A method for selecting a bovine individual which has a high resistance to the onset of leukemia caused by bovine leukemia virus BLV, which comprises:

(1) amplifying a genome DNA isolated from a bovine individual by polymerase chain reaction (PCR) using DRB40 or DRB100 as a forward primer and SRB3 as a reverse primer to prepare a PCR product containing a DNA coding for a part or full length of β1 domain of bovine MHC Class II DRβ chain, and (2) judging that the bovine individual, in which the PCR product is not digested by PstI and DraIII, has a high resistance to the onset of the leukemia.

* * * * *

UNITED STATES PATENT AND TRADEMARK OFFICE
CERTIFICATE OF CORRECTION

PATENT NO. : 6,815,158 B2
DATED : November 9, 2004
INVENTOR(S) : Y. Aida

It is certified that error appears in the above-identified patent and that said Letters Patent is hereby corrected as shown below:

Title page,
Item [56], References Cited, U.S. PATENT DOCUMENTS, was omitted and should be included:
-- 6,284,457    09/04/01    Aida --
FOREIGN PATENT DOCUMENTS, was omitted and should be included:
-- 0906947    12/01/99    I.P.O. --
-- 93/19204   09/30/93    W.I.P.O. --
OTHER PUBLICATIONS, the following were omitted and should be included:
-- AIDA et al., "Identification of Tumor-Associated Antigen that is Expressed on Bovine Leukemia Virus-Induced Lymphosarcoma Cells and Expression of its Human Homologue in Human T-cell Lymphotrophic Virus I-infected Cell Lines", Leukemia, Vol. 8, pp.231-234 (1994).
KOGUCHI et al., "Changes in the Distribution of cells Expressing Tumor-Associated Antigen in Lymph Nodes during the progression of Enzootic Bovine Leukosis" J. Compara Pathol. Vol. 115, pp. 343-352 (1996). --

Signed and Sealed this

Twenty-eighth Day of June, 2005

JON W. DUDAS
*Director of the United States Patent and Trademark Office*